(12) United States Patent
Rosa et al.

(10) Patent No.: US 10,973,599 B2
(45) Date of Patent: Apr. 13, 2021

(54) SURGICAL PLATFORM SUPPORTED BY MULTIPLE ARMS

(71) Applicant: Intuitive Surgical Operations, Inc., Sunnyvale, CA (US)

(72) Inventors: David J. Rosa, San Jose, CA (US); Gary S. Guthart, Los Altos, CA (US); Simon P. DiMaio, San Carlos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 65 days.

(21) Appl. No.: 16/088,413

(22) PCT Filed: Mar. 16, 2017

(86) PCT No.: PCT/US2017/022667
§ 371 (c)(1),
(2) Date: Sep. 25, 2018

(87) PCT Pub. No.: WO2017/165183
PCT Pub. Date: Sep. 28, 2017

(65) Prior Publication Data
US 2020/0297443 A1  Sep. 24, 2020

Related U.S. Application Data

(60) Provisional application No. 62/313,599, filed on Mar. 25, 2016, provisional application No. 62/313,590, filed on Mar. 25, 2016.

(51) Int. Cl.
*A61B 34/00* (2016.01)
*A61B 34/37* (2016.01)
(Continued)

(52) U.S. Cl.
CPC .............. *A61B 34/70* (2016.02); *A61B 34/35* (2016.02); *A61B 34/37* (2016.02); *B25J 9/0009* (2013.01);
(Continued)

(58) Field of Classification Search
CPC ......... A61B 34/70; A61B 34/35; A61B 34/37; A61B 2034/304; A61B 2034/301;
(Continued)

(56) References Cited

U.S. PATENT DOCUMENTS 4,806,068 A * 2/1989 Kohli ......................... B25J 9/04
414/735
5,053,687 A * 10/1991 Merlet ..................... F16H 21/46
318/568.2
(Continued)

FOREIGN PATENT DOCUMENTS

CN         102917662 A      2/2013
WO     WO-2006124390 A2   11/2006
(Continued)

OTHER PUBLICATIONS

International Search Report and Written Opinion for Application No. PCT/US2017/022667, dated Jun. 7, 2017, 13 pages.
(Continued)

*Primary Examiner* — Julian W Woo
(74) *Attorney, Agent, or Firm* — Fish & Richardson P.C.

(57) ABSTRACT

A surgical module is supported by manipulators that are removably attached to the surgical module. The surgical module may enable operation of surgical tools by providing an integration between actuating mechanisms of the manipulators and actuating mechanisms of the surgical tools. Alternatively or additionally, the surgical module may enable
(Continued)

operation of the surgical tools by providing physical access for deploying surgical tools that are operatively connected to the manipulators.

21 Claims, 15 Drawing Sheets

(51) Int. Cl.
  *A61B 34/35* (2016.01)
  *B25J 9/06* (2006.01)
  *B25J 9/00* (2006.01)
  *B25J 9/16* (2006.01)
  *A61B 34/20* (2016.01)
  *A61B 34/30* (2016.01)

(52) U.S. Cl.
  CPC ............... *B25J 9/06* (2013.01); *B25J 9/1602* (2013.01); *A61B 2034/2074* (2016.02); *A61B 2034/301* (2016.02); *A61B 2034/304* (2016.02)

(58) Field of Classification Search
  CPC ............ A61B 2034/2074; B25J 9/0009; B25J 9/1602; B25J 9/06
  See application file for complete search history.

(56) References Cited

U.S. PATENT DOCUMENTS

| | | | | |
|---|---|---|---|---|
| 5,808,665 | A * | 9/1998 | Green | H04N 13/398 348/65 |
| 6,041,500 | A * | 3/2000 | Terpstra | B23P 15/006 29/23.51 |
| 6,047,610 | A * | 4/2000 | Stocco | B25J 17/0266 74/479.01 |
| 6,246,200 | B1 * | 6/2001 | Blumenkranz | B25J 9/1689 128/DIG. 7 |
| 6,557,432 | B2 * | 5/2003 | Rosheim | B25J 17/0266 403/203 |
| 6,788,018 | B1 * | 9/2004 | Blumenkranz | B25J 9/0018 128/DIG. 7 |
| 7,725,214 | B2 | 5/2010 | Diolaiti | |
| 7,955,322 | B2 | 6/2011 | Devengenzo et al. | |
| 8,134,324 | B2 * | 3/2012 | Nishida | G05B 15/02 318/568.21 |
| 8,491,603 | B2 | 7/2013 | Yeung et al. | |
| 8,529,582 | B2 | 9/2013 | Devengenzo et al. | |
| 8,666,544 | B2 | 3/2014 | Moll et al. | |
| 8,801,661 | B2 | 8/2014 | Moll et al. | |
| 8,834,489 | B2 | 9/2014 | Cooper et al. | |
| 9,109,743 | B2 * | 8/2015 | Schwab | B25J 17/0266 |
| 10,376,338 | B2 * | 8/2019 | Taylor | B25J 9/009 |
| 2010/0241137 | A1 | 9/2010 | Doyle et al. | |
| 2011/0160745 | A1 * | 6/2011 | Fielding | A61B 34/37 606/130 |
| 2013/0144307 | A1 | 6/2013 | Jeong et al. | |
| 2013/0296882 | A1 | 11/2013 | Kim et al. | |

FOREIGN PATENT DOCUMENTS

| | | |
|---|---|---|
| WO | WO-2010041900 A2 | 4/2010 |
| WO | WO-2011100125 A1 | 8/2011 |
| WO | WO-2011115387 A2 | 9/2011 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 17770845 dated Oct. 18, 2019, 8 pages.

* cited by examiner

SURGICAL PLATFORM SUPPORTED BY MULTIPLE ARMS

RELATED APPLICATIONS

This patent application claims priority to, and the filing date benefit of, U.S. Provisional Patent Applications No. 62/313,590 (filed Mar. 25, 2016) and 62/313,599 (filed Mar. 25, 2016), both of which are incorporated by reference herein in their entirety.

BACKGROUND

The present disclosure relates generally to medical and robotic devices, systems, and methods.

Minimally invasive medical techniques typically reduce the amount of extraneous tissue that is damaged during diagnostic or surgical procedures, thereby reducing patient recovery time, discomfort, and deleterious side effects. Because the average hospital stay for a standard surgery is typically significantly longer than the average stay for an analogous minimally invasive surgery, increased use of minimally invasive techniques can substantially reduce hospital costs each year.

While many of the surgeries performed each year in the United States could potentially be performed in a minimally invasive manner, only a portion of the current surgeries use these advantageous techniques due to limitations in minimally invasive surgical instruments and the additional surgical training involved in mastering them. Thus, there is a need for improved devices, systems and related methods for minimally invasive surgery.

SUMMARY

Certain embodiments enable improved operation of surgical tools through a surgical module that is supported by manipulators that are removably attached to the surgical module. The surgical module may enable operation of the surgical tools by providing an integration between actuating mechanisms of the manipulators and actuating mechanisms of the surgical tools. Alternatively or additionally, the surgical module may enable operation of the surgical tools by providing physical access for deploying surgical tools that are operatively connected to the manipulators.

In accordance with one embodiment, a computer-assisted medical system comprises a surgical module, a plurality of manipulator assemblies, and an input controller. The surgical module includes a plurality of actuating mechanisms configured to control one or more surgical tools. The plurality of manipulator assemblies are configured to support and control the surgical module, each manipulator assembly of the plurality of manipulator assemblies being removably attached to the surgical module at a distal portion of that manipulator assembly, and the distal portion of that manipulator assembly including an actuating mechanism configured to interface with one of the plurality of actuating mechanisms of the surgical module. The input controller is operatively coupled to the plurality of manipulator assemblies via a processor and configured to control the manipulator assemblies and the one or more surgical tools through the actuating mechanisms of the plurality of manipulator assemblies.

Another embodiment relates to a method of operating a computer-assisted medical system. A first operation includes using a plurality of manipulator assemblies to support and control a surgical module, the surgical module including a plurality of actuating mechanisms configured to control one or more surgical tools, and each manipulator assembly of the plurality of manipulator assemblies being removably attached to the surgical module at a distal portion of that manipulator assembly, the distal portion of that manipulator assembly including an actuating mechanism configured to interface with one of the plurality of actuating mechanisms of the surgical module. A second operation includes controlling, via a processor, the manipulator assemblies and the one or more surgical tools through the actuating mechanisms of the plurality of manipulator assemblies.

In accordance with another embodiment, a computer-assisted medical system comprises a surgical module, a plurality of manipulator assemblies, and an input controller. The surgical module includes a plurality of channels (e.g., including hollow tubes) configured to deploy a plurality of surgical tools. The plurality of manipulator assemblies are configured to support the surgical module, each manipulator assembly of the plurality of manipulator assemblies being operatively connected to a corresponding surgical tool of the plurality of surgical tools, and each manipulator assembly of the plurality of manipulator assemblies being removably attached to the surgical module at a distal portion of that manipulator assembly. The input controller is operatively coupled to the plurality of manipulator assemblies via a processor and configured to control the manipulator assemblies and the one or more surgical tools through the actuating mechanisms of the plurality of manipulator assemblies.

Another embodiment relates to a method of operating a computer-assisted medical system. A first operation includes using a plurality of manipulator assemblies to support a surgical module, the surgical module including a plurality of channels configured to deploy a plurality of surgical tools, each manipulator assembly of the plurality of manipulator assemblies being operatively connected to a corresponding surgical tool of the plurality of surgical tools, and each manipulator assembly of the plurality of manipulator assemblies being removably attached to the surgical module at a distal portion of that manipulator assembly. A second operation includes controlling, via a processor, the plurality of manipulator assemblies and the plurality of surgical tools through actuating mechanisms of the plurality of manipulator assemblies, the plurality of surgical tools being deployed via the plurality of channels of the surgical module.

Another embodiment relates to an apparatus for carrying out any one of the above-described methods, where the apparatus includes a computer for executing instructions related to the method. For example, the computer may include a processor for executing at least some of the instructions. Additionally or alternatively the computer may include circuitry or other specialized hardware for executing at least some of the instructions. In some operational settings, the apparatus may be configured as a system that includes one or more units, each of which is configured to carry out some aspects of the method either in software, in hardware or in some combination thereof. At least some values for the results of the method can be saved for later use in a computer-readable medium, including memory units and storage devices. Another embodiment relates to a computer-readable medium that stores (e.g., tangibly embodies) a computer program for carrying out the any one of the above-described methods with a computer. In these ways aspects of the disclosed embodiments enable improved integration between actuating mechanisms of manipulators and actuating mechanisms of one or more surgical tools.

BRIEF DESCRIPTION OF DRAWINGS

Certain embodiments are illustrated by way of example and not limitation in the figures of the accompanying drawings.

DETAILED DESCRIPTION

Figure 1:
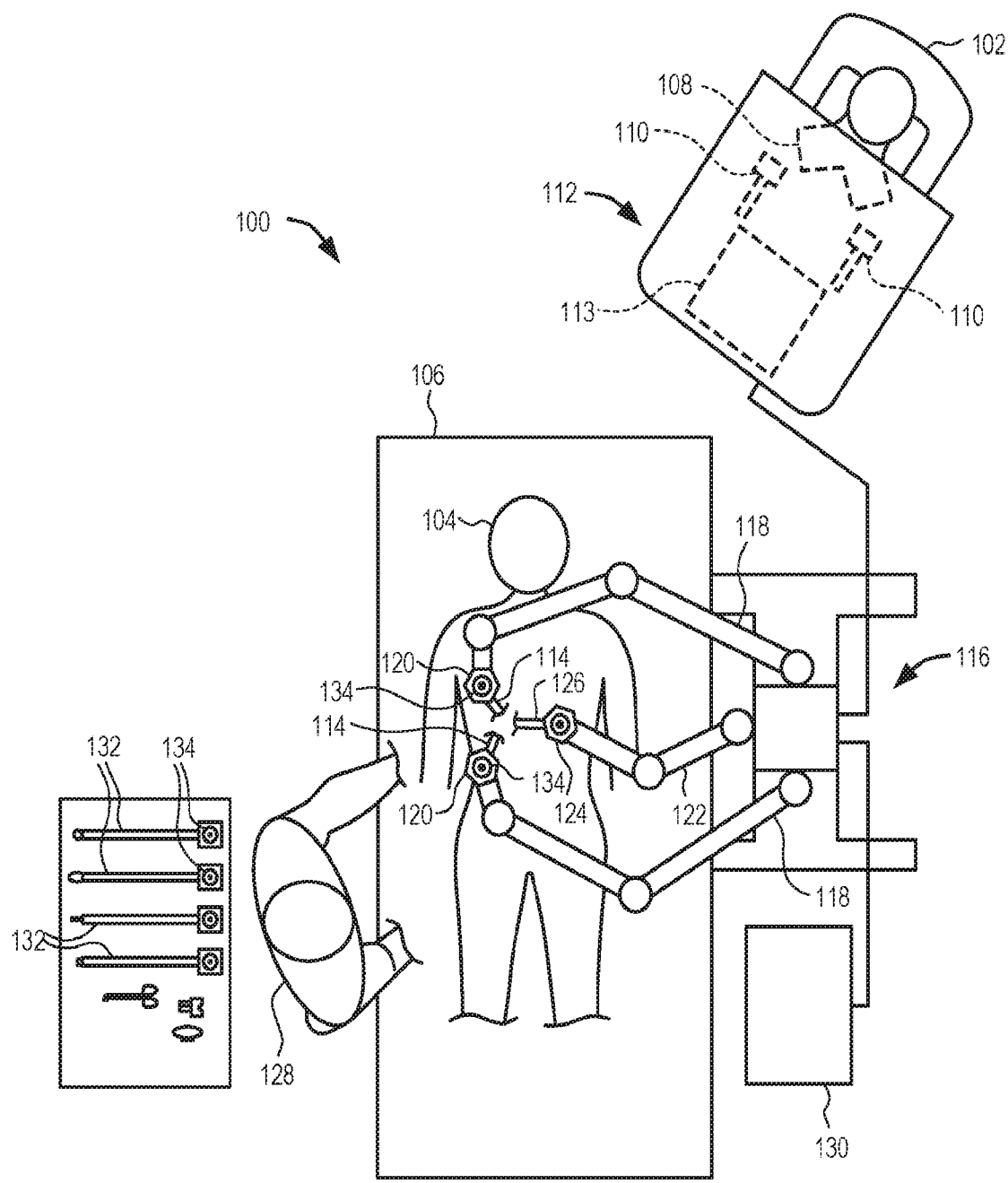
FIG. 1 is a schematic plan view illustrating an exemplary robotic surgical system, including a master surgeon console (also called a workstation) for inputting a surgical procedure and a robotic manipulator system for robotically moving surgical instruments at a surgical site within a patient.

The description that follows includes systems, methods, techniques, instruction sequences, and computer-program products that illustrate embodiments of the present disclosure. In the following description, for purposes of explanation, numerous specific details are set forth in order to provide an understanding of various embodiments of the disclosed subject matter. It will be evident, however, to those skilled in the art that embodiments of the disclosed subject matter may be practiced without these specific details. In general, well-known instruction instances, protocols, structures and techniques have not been shown in detail.

Minimally invasive robotically-assisted surgical or telesurgical systems have been developed to increase a surgeon's dexterity and to avoid some of the limitations on manual minimally invasive surgical/interventional techniques. In telesurgery, sitting at a surgeon console/workstation, the surgeon remotely controls and manipulates surgical instrument movements, rather than directly holding and moving the instruments by hand. The surgeon is provided with an image of the surgical site at the surgeon workstation. While viewing a two or three dimensional image of the surgical site on a display, the surgeon performs the surgical procedures on the patient by manipulating master control/input devices (also called the master or input controller), which in turn control motion of the servo-mechanically operated instruments.

The surgeon typically operates the master controller from a location that may be remote from the patient (e.g., across the operating room, in a different room, or a completely different building from the patient). The master controller usually includes one or more hand input devices, such as hand-held wrist gimbals, joy-sticks, exoskeletal gloves, or the like, which are operatively coupled to the surgical instruments that are releasably coupled to a patient side surgical manipulator assembly (also called the slave(s)). The slave is an electro-mechanical assembly that includes a one or more arms, joints, linkages, servo motors, etc. connected together to support and control one or more surgical instruments. In a surgical procedure, the surgical instruments (including an endoscope) may be introduced directly into an open surgical site or more typically through trocar sleeves into a body cavity. Depending on a surgical procedure, there are available a variety of surgical instruments, such as tissue graspers, needle drivers, electrosurgical cautery probes, etc., to perform various functions for the surgeon, e.g., holding or driving a needle, suturing, grasping a blood vessel, or dissecting, cauterizing or coagulating tissue. The slave may be a multi-port robot as exemplary demonstrated in U.S. Pat. No. 6,331,181 (filed Oct. 15, 1999), a single-port robot as exemplary demonstrated in U.S. Pat. No. 8,784,435 (filed Aug. 12, 2010), or a flexible robot as exemplary demonstrated in U.S. Pat. No. 8,801,661 (filed Nov. 7, 2013). The full disclosure of U.S. Pat. Nos. 6,331,181, 8,784,435, and 8,801,661 are herein incorporated by referenced for all purposes.

A surgical manipulator assembly may be said to be divided into three main components that include a non-sterile drive and control component, a sterilizable end effector or surgical tool/instrument, and an interface. The interface includes electro-mechanical as well as required software for coupling the surgical tool with the drive and control component, and for transferring motion from the drive component to the surgical tool. Typically a surgeon will require different surgical instruments/tools during a procedure. As such, these surgical instruments will likely be attached and detached from the manipulator arm a number of times during an operation.

FIG. 1 illustrates, as an example, components of a multi-port robotic surgical system 100 for performing minimally invasive robotic surgery. System 100 is similar to that described in more detail in U.S. Pat. No. 6,246,200 (filed Aug. 3, 1999), the full disclosure of which is incorporated herein by reference. Further related details are described in U.S. Pat. No. 8,529,582 (filed May 20, 2011) and U.S. Pat. No. 8,823,308 (filed Jul. 1, 2011), the full disclosures of which are likewise incorporated herein by reference. A system operator 102 (generally a surgeon) performs a minimally invasive surgical procedure on a patient 104 lying on an operating table 106. The system operator 102 sees images presented by display 108 and manipulates one or more input devices (or masters) 110 at a surgeon's console (or workstation) 112. In response to the surgeon's input commands, a computer processor 113 of console 112 directs movement of surgical tools 114 (also called instruments 114), effecting servo-mechanical movement of the instruments via a robotic patient-side surgical manipulator assembly 116 (a cart-based system in this example) including joints, linkages, and manipulator arms each having a telescopic insertion axis. In one embodiment, processor 113 correlates the movement of the end effectors of tools 114 so that the motions of the end effectors follow the movements of the input devices in the hands of the system operator 102.

Processor 113 will typically include data processing hardware and software, with the software typically comprising machine-readable code. The machine-readable code will embody software programming instructions to implement some or all of the methods described herein. While processor 113 is shown as a single block in the simplified schematic of FIG. 1, the processor may comprise a number of data processing circuits, with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein.

In one example, manipulator assembly 116 includes at least four robotic manipulators. Three linkages 118 (mounted at the sides of the cart in this example) support and position manipulators 120 with linkages 118 in general supporting a base of the manipulators 120 at a fixed location during at least a portion of the surgical procedure. Manipulators 120 move surgical tools 114 for robotic manipulation of tissues. One additional linkage 122 (mounted at the center of the cart in this example) supports and positions manipulator 124 which controls the motion of an endoscope/camera probe 126 to capture an image (preferably stereoscopic) of the internal surgical site. The fixable portion of positioning linkages 118, 122 of the patient-side system is sometimes referred to herein as a "set-up arm". It should be clear to a person of ordinary skill in the art that linkages 118 can also be mounted to operating table 106 or to the ceiling.

In one example, the image of the internal surgical site is shown to operator 102 by a stereoscopic display 108 in surgeon's console 112. The internal surgical site is simultaneously shown to assistant 128 by an assistance display 130.

Assistant 128 assists in pre-positioning manipulator assemblies 120 and 124 relative to patient 104 using set-up linkage arms 118, 122; in swapping tools 114 from one or more of the surgical manipulators for alternative surgical tools or instruments 132; in operating related non-robotic medical instruments and equipment; in manually moving a manipulator assembly so that the associated tool accesses the internal surgical site through a different aperture, and the like.

In general terms, the linkages 118, 122 are used primarily during set-up of patient-side system 6 (also called manipulator system 6), and typically remain in a fixed configuration during at least a portion of a surgical procedure. Manipulators 120, 124 each comprise a driven linkage which is actively articulated under the direction of surgeon's console 112. Although one or more of the joints of the set-up arm may optionally be driven and robotically controlled, at least some of the set-up arm joints may be configured for manual positioning by assistant 128.

For convenience, a manipulator such as manipulator 120 that is supporting a surgical tool used to manipulate tissues is sometimes referred to as a patient-side manipulator (PSM), while a manipulator 124 which controls an image capture or data acquisition device such as endoscope 126 may be referred to as an endoscopic-camera manipulator (ECM). The manipulators may optionally actuate, maneuver, and control a wide variety of instruments or tools, image capture devices, and the like which are useful for surgery.

Tools 114 and endoscope 126 may be manually positioned when setting up for a surgical procedure, when reconfiguring the manipulator system 6 for a different phase of a surgical procedure, when removing and replacing an instrument with an alternate instrument 132, and the like. During such manual reconfiguring of the manipulator assembly by assistant 128, the manipulator assembly may be placed in a different mode than is used during master/slave telesurgery, with the manually repositionable mode sometimes being referred to as a clutch mode. The manipulator assembly may change between the tissue manipulation mode and the clutch mode in response to an input such as pushing a button or switch on manipulator 120, or some other component to the manipulator assembly, thereby allowing assistant 128 to change the manipulator mode.

As can be seen in FIG. 1, indicators 134 may be disposed on a manipulator assembly. In this embodiment, indicators 134 are disposed on manipulators 120 near the interface between the manipulators and their mounted tools 114. In alternative embodiments, indicators 134 may instead be disposed on set-up arms 118, 122, on tools 114, elsewhere on manipulators 120, 124, or the like. An example of an indicator is disclosed in U.S. Pat. No. 8,273,076 (filed Nov. 3, 2006), the full disclosure of which is incorporated herein by reference.

Figure 2:
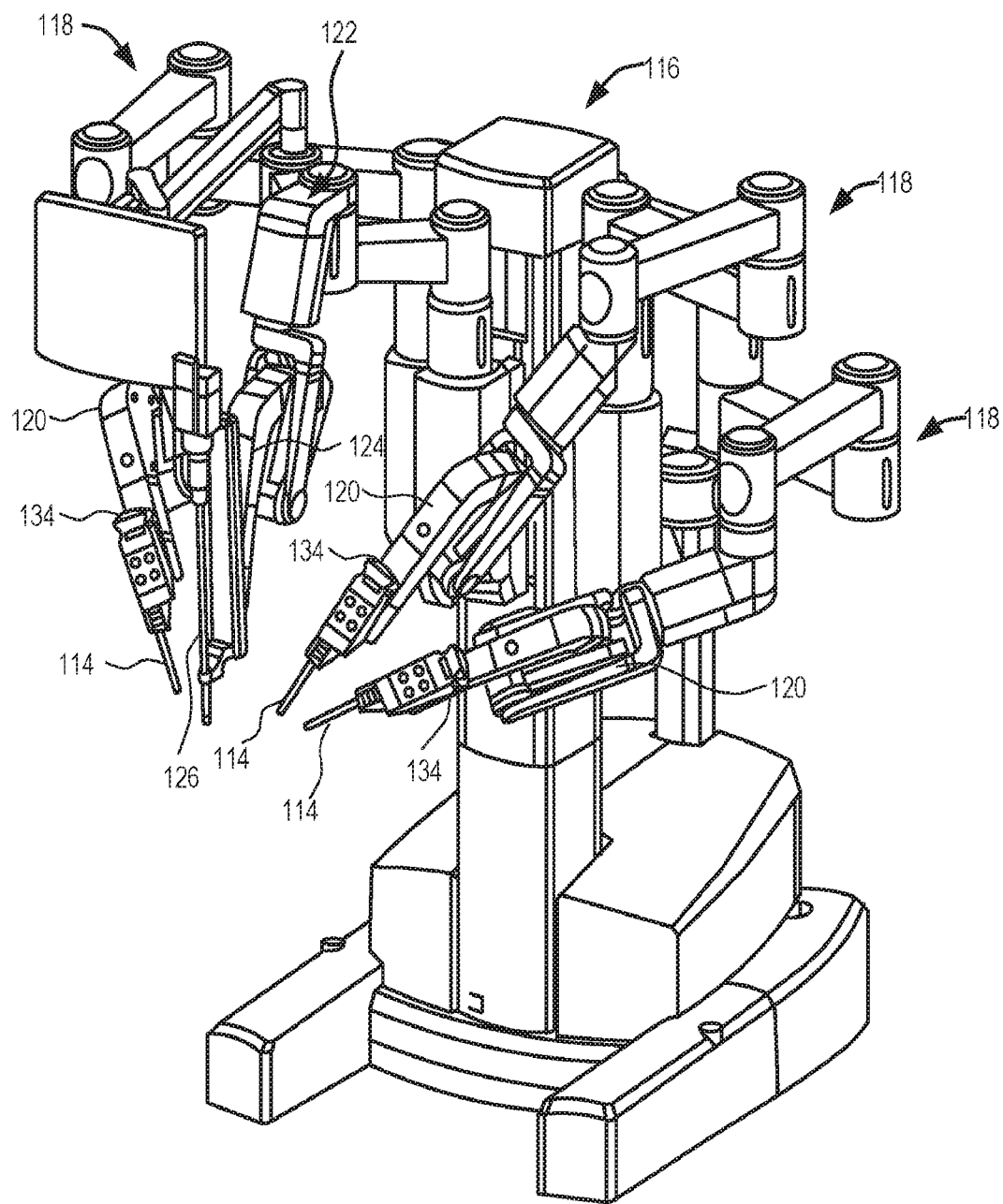
FIG. 2 is a perspective view that shows an exemplary surgical station having a plurality of robotic manipulators for robotically moving surgical instruments.

FIG. 2 illustrates an embodiment of multi-port robotic patient-side surgical manipulator assembly 116 which is commercialized by Intuitive Surgical, Inc., Sunnyvale, Calif. As shown, surgical manipulator assembly 116 includes four robotic manipulators supported by a mobile cart. Another embodiment of multi-port robotic patient-side surgical manipulator assembly 116 may involve four robotic manipulators individually supported by four mobile carts. Yet another embodiment of multi-port robotic patient-side surgical manipulator assembly 116 may involve supporting structure for attaching it to an operating bed or ceiling.

Examples of single-port and flexible robotic patient side surgical manipulator assemblies are shown and described in U.S. Pat. Nos. 8,784,435 and 8,801,661, respectively. From these descriptions, the patient-side surgical manipulator assemblies for prior art multi-port robotically assisted systems, single-port robotically assisted systems, and flexible robotically assisted system are substantially different from one another that they require separate designs, developments, and manufacturing lines. In addition to added manufacturing costs and complexities for the manufacturer, hospitals are required to purchase separate patient-side surgical manipulators for multi-port, single-port, and flexible medical procedures, which increases the costs for medical robotic procedures. At a time when health care costs are undergoing strict scrutiny, any added costs are not desirable.

Figure 3:
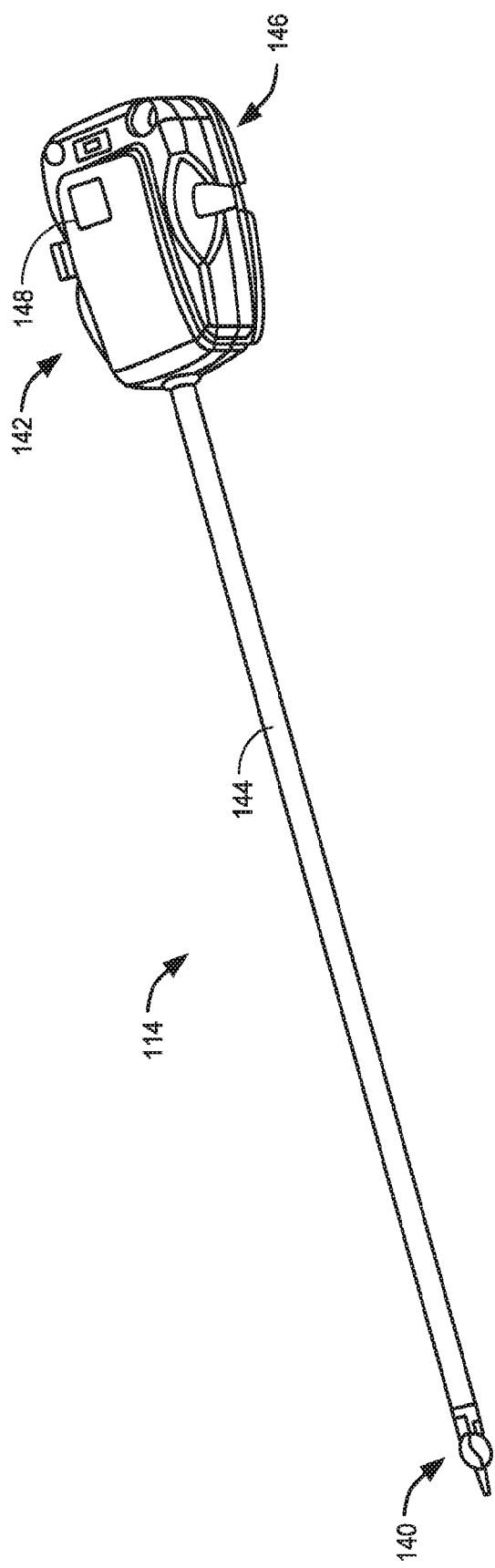
FIG. 3 is a perspective view of an example of a surgical instrument for use in the system of FIG. 1.

FIG. 3 shows a surgical tool (or instrument) 114 that includes a surgical end effector 140 supported relative to a housing 142 by an intermediate portion of the instrument, the intermediate portion often comprising of an elongate shaft 144. End effector 140 may be supported relative to the shaft by a distal joint or wrist so as to facilitate orienting the end effector within an internal surgical workspace. Proximal housing 142 will typically include an interface 146 adapted for coupling to a holder of a manipulator 120. As described in more detail in U.S. Pat. No. 6,331,181 (filed Oct. 15, 1999), the full disclosure of which is incorporated herein by reference, tool 114 will often include a memory 148, with the memory typically being electrically coupled to a data interface (the data interface typically forming a portion of interface 146). This allows data communication between memory 148 and the robotic surgical processor 113 of console 112 (see FIG. 1) when the instrument is mounted on the manipulator.

A variety of alternative robotic surgical instruments of different types and differing end effectors 140 may be used, with the instruments of at least some of the manipulators being removed and replaced during a surgical procedure. Additional details are provided in U.S. Pat. No. 8,823,308.

In some operational settings, the above-described tools 114 and end effectors 140 can be combined into combinations with multiple capabilities. Additional details related to these combinations are provided in U.S. Pat. No. 7,725,214 (filed Jun. 13, 2007), the disclosure of which is incorporated herein by reference in its entirety. Details related to interfaces between the tools 114 and the manipulators 120 are provided in U.S. Pat. No. 7,955,322 (filed Dec. 20, 2006), U.S. Pat. No. 8,666,544 (filed Jul. 10, 2013), and U.S. Pat. No. 8,529,582, the disclosure of each of which is incorporated herein by reference in its entirety.

Figure 4:
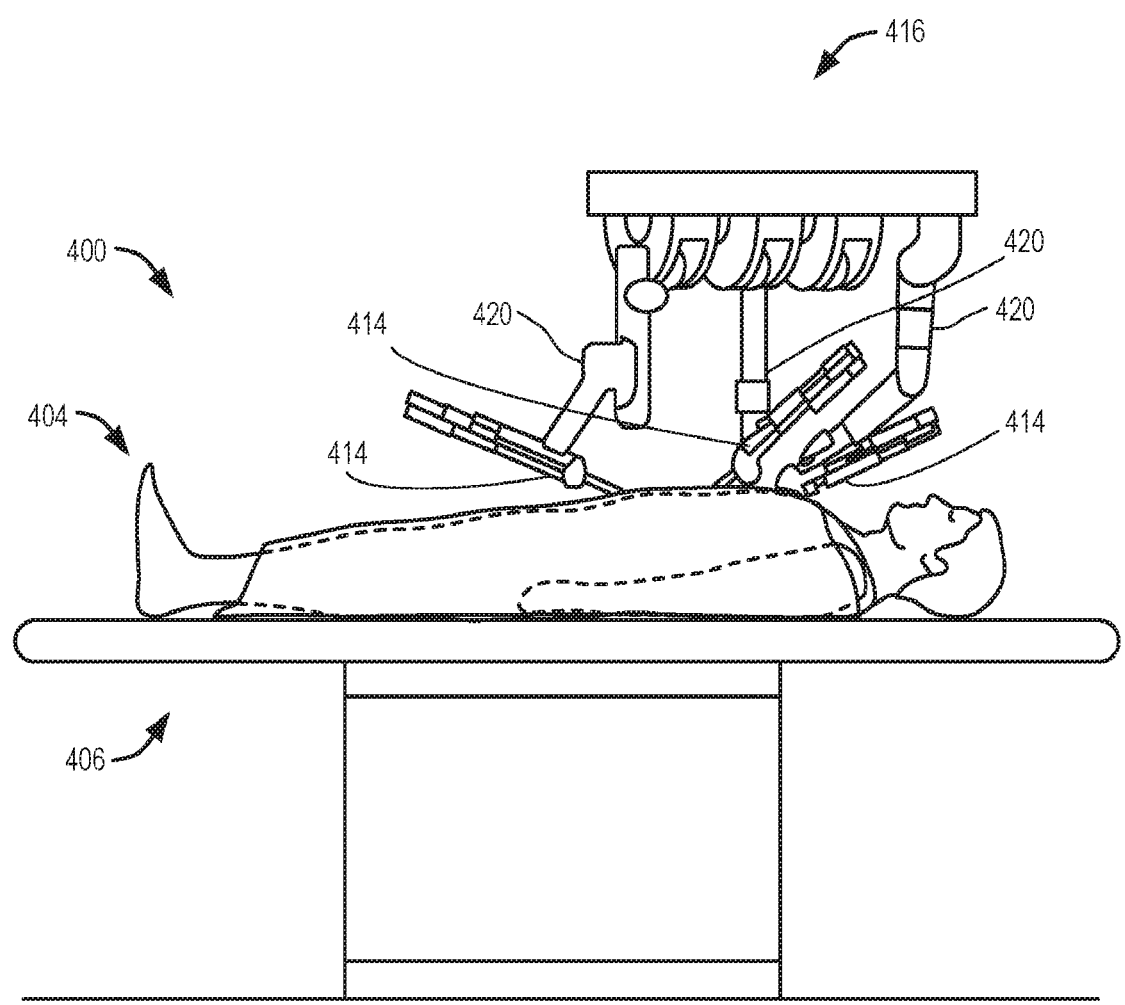
FIG. 4 is a side view of an embodiment of a manipulator system.

FIG. 4 shows a simplified side view of a surgical station 400 that is related to the embodiment of FIG. 1. Similarly as in the FIG. 1, a patient 404 is supported by a table 406 adjacent to a manipulator system 416, the support for which is not shown. The manipulator system 416, which supports three manipulators 420 with associated tools 414, will typically remain in a fixed location over patient 404 during at least a portion of a surgical procedure.

Figure 5:
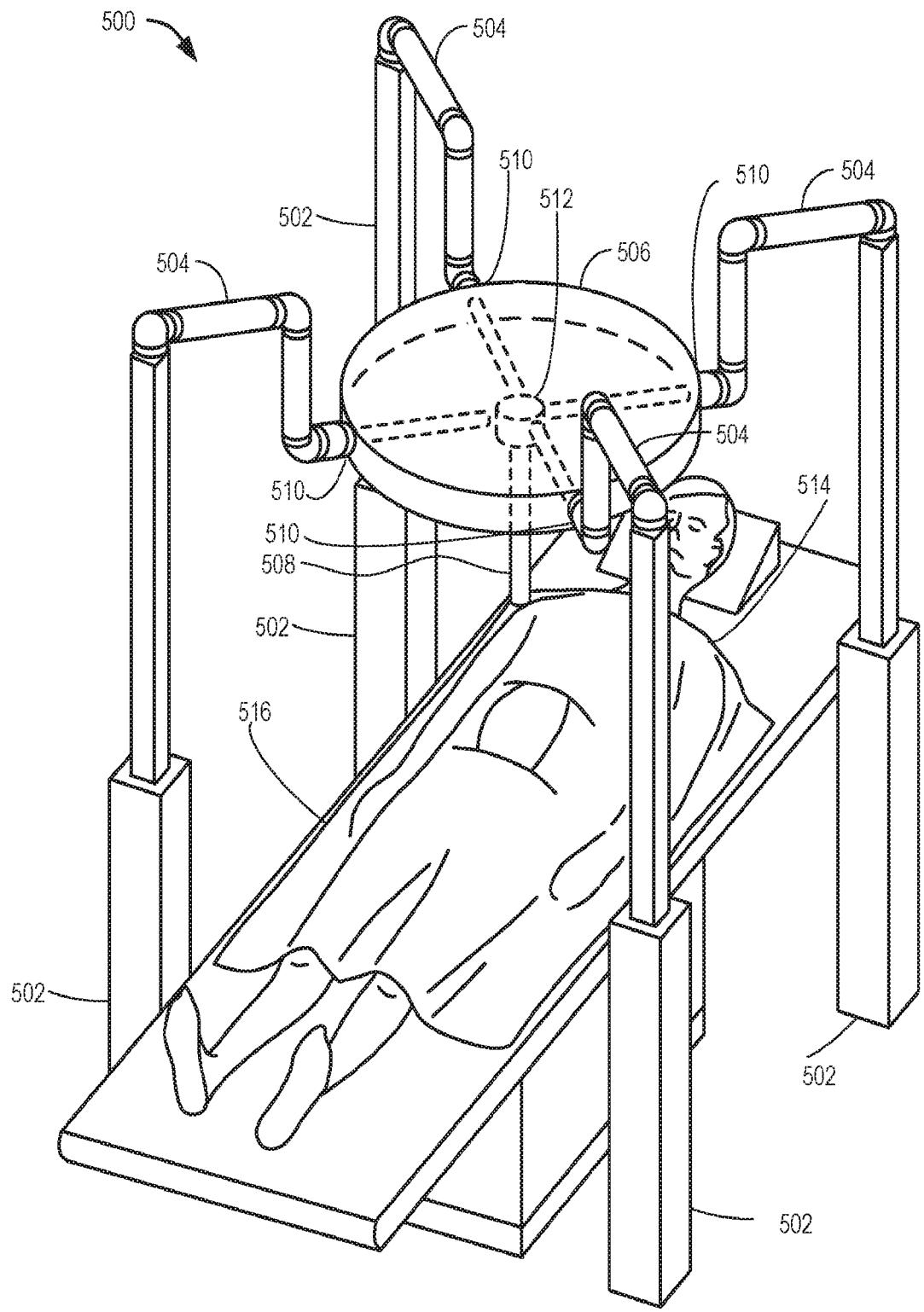
FIG. 5 is a perspective view of a surgical system in accordance with an example embodiment.
Figure 6:
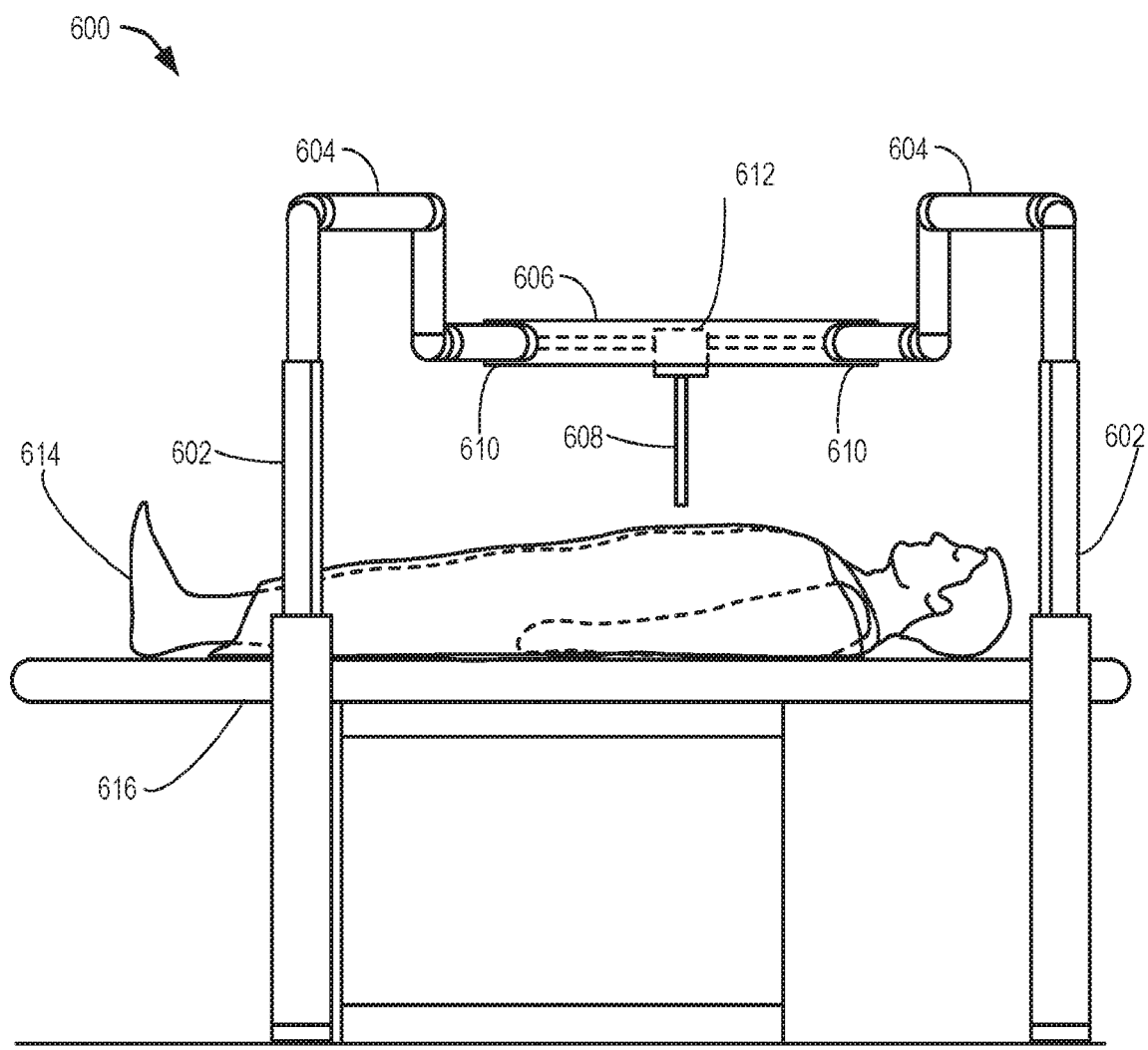
FIG. 6 is a side view of a surgical system in accordance with another example embodiment.

In the above-disclosed embodiments, each surgical tool 114 is supported by a single manipulator 120. FIGS. 5-6 disclose aspects of example embodiments of the current invention where a plurality of manipulators of the same type support a single surgical module through which one or more surgical tools are deployed. In an aspect of the current invention, the manipulators 120 are configured to be used in multi-port robotically assisted minimally invasive procedures (e.g., where each manipulator supports surgical tool 114), in single-port robotically assisted minimally invasive procedures (e.g., where two or more of the manipulators support a single surgical module for single-port surgery), and in flexible robotically assisted minimally invasive procedures (e.g., where two or more of the manipulators support a single surgical module configured for flexible minimally invasive procedures). In so doing, less design, development, and manufacturing resources, and hence less costs, are needed to design and build manipulators 120 because the same manipulators are then configured and used for use in multi-port, single-port, and flexible robotically assisted minimally invasive procedures.

FIG. 5 shows a perspective view of a portion of a surgical system 500 in accordance with an example embodiment. With reference to the system 100 of FIG. 1, the single manipulator assembly 116 that supports multiple manipulators 120 has been "separated" into a plurality of four separate manipulators 504 (also called manipulator assemblies 504). As shown, the manipulators 504 are mounted to the floor at manipulator support structures 502. But, it should be clear to a person of ordinary skill in the art that the manipulators 504 may each be mounted on its own cart, to the operating table, or to the ceiling. Although the manipulator support structures 502 and manipulators 504 are represented as simplified structures, the more detailed representations of the previous figures are fully applicable. The four manipulators 504 support a surgical module 506 that includes actuating mechanisms that are configured to control one or more surgical tools 508, possibly enclosed by a sheath, through actuating mechanisms of the manipulators 504. In operation, an input controller (e.g., at console 112) is operatively coupled to the manipulators 504 and configured to control the manipulators 504 and one or more surgical tools 508 through the actuating mechanisms of the manipulators 504.

In FIG. 5, a distal portion 510 of each manipulator 504 removably attaches to the surgical module 506 so that an actuating mechanism of each manipulator 504 interfaces with a corresponding actuating mechanism of the surgical module 506, in accordance with interfaces discussed above with respect to FIGS. 1-3 and related patents (e.g., U.S. Pat. Nos. 7,955,322, 8,666,544, 8,529,582, 7,725,214, and 8,801,661). That is, the previously discussed interfaces between the manipulators 120 and the surgical tools 114 are replaced by equivalent interfaces between the manipulators 504 and the surgical module 506, which includes an integration unit 512 that combines the contributions of the actuating mechanisms of the manipulators 504 for controlling the one or more surgical tools 508. Optionally, other interface designs may be used, such as interfaces that use levers, sliders, gimbals, gears, and the like. In addition to controlling the deployment of the one or more surgical tools 508, the manipulator systems 502 provide physical support for the surgical module 506 and control the position and orientation of the surgical module 506 with respect to a patient 514 on a surgical table 516. Although this embodiment includes four manipulators 504, other configurations with a different number of manipulators (e.g., two, three, five, or more) are possible depending on the requirements of the operational setting.

Actuating force or torque from a manipulator is mechanically transmitted through the surgical module to an instrument interface on the integration unit, to which an instrument is mounted, and so the manipulator drives the instrument via the surgical module and its integration unit. Thus if two manipulators support the surgical module, up to two instruments mounted to the integration unit may be driven. Likewise if three manipulators support the surgical module, up to three instruments mounted to the integration unit may be driven, and so on for four, five, or more driving manipulators and corresponding driven instruments. In some implementations, actuating force or torque from two or more manipulators is mechanically transmitted through the surgical module to a single instrument interface on the integration unit, to which a single instrument is mounted, and so the two manipulators drive the single instrument via the surgical module and its integration unit. Likewise, three, four, five, or more manipulators may drive a single instrument. And, a single surgical module may optionally include one or more one-to-one manipulator to instrument drives and one or more plurality-to-one instrument drives. The mechanical coupling to transmit actuating force or torque between the actuation input received at driven interface on the surgical module and the corresponding drive interface on the integration unit is optionally any of various well-known mechanical actuation links, such as rotating or translating rods, gears, universal or constant velocity joints, levers, cables, and the like.

The use of compatible or equivalent interfaces as described above enables a manipulator 504 to be used in combination with either an operatively connected surgical tool (e.g., as in FIG. 2) or the surgical module 506 of FIG. 5. Other aspects related to these interfaces may be applied to the surgical modules. For example, the manipulators 504 may be draped with a sterile drape or sterilized. Likewise, the surgical module 506 may be draped with a sterile drape or sterilized. Sterile adapters may be used between actuation interfaces of the manipulators 504 and the surgical module 506. Sterile adapters may be used between actuation interfaces of the surgical module 506 and the surgical tools 508. However, if the surgical module 506 is sterilizable, then no sterile adapter is generally needed between the surgical module 506 and the surgical tools 508. Further related details can be found, for example, in U.S. Pat. Nos. 7,955,322, 8,666,544, 8,529,582, 7,725,214, and 8,801,661, all of which are incorporated by reference herein.

FIG. 6 shows a side view of a surgical system 600 for an embodiment with two manipulator systems 602 (e.g., a manipulator assembly), each supporting a separate manipulator 604. Similarly as in the system 500 of FIG. 5, manipulator systems 602 and manipulators 604 are shown as simplified structures, and the more detailed representations of the previous figures are fully applicable.

Similarly as in the previous figure, FIG. 6 also shows a surgical module 606 that includes actuating mechanisms that are configured to control one or more surgical tools 608, possibly enclosed by a sheath, through actuating mechanisms of the manipulators 604. A distal portion 610 of each manipulator 604 removably attaches to the surgical module 606 so that an actuating mechanism of that manipulator 604 interfaces with a corresponding actuating mechanism of the surgical module 606 in correspondence to interfaces discussed above with respect to FIGS. 1-3. In addition to controlling the deployment of the one or more surgical tools 608, the manipulator systems 502 provide physical support for the surgical module 606 and control the position and orientation of the surgical module 606 with respect to a patient 614 on a surgical table 616.

Additional embodiments are discussed below for structural modifications related to the manipulators 504 and the tools 508 of FIG. 5 (and corresponding elements of FIG. 6).

Figure 7:
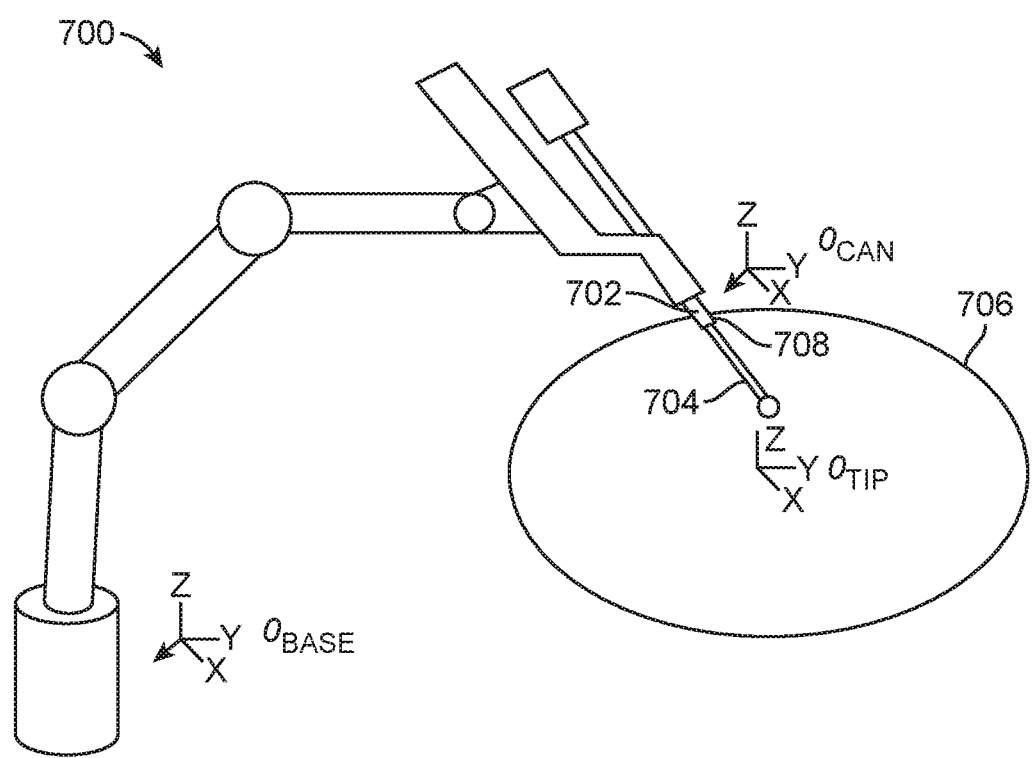
FIG. 7 is a diagram of a software-center manipulator assembly in accordance with an example embodiment.

FIG. 7 shows a software-center manipulator assembly 700, which may be adapted for one or more of the manipulators 504 in accordance with an example embodiment. (With a software-center manipulator, a center of rotational motion (e.g., pitch, yaw, and roll of the instrument shaft) may be defined at a point on the instrument shaft that remains stationary in space under software control. With a software-center manipulator, it is possible to remove the rotational center of motion constraint during operation, and so move the manipulator to various poses in space without constraint. This is in contrast to a hardware-center manipulator in which the center of rotational motion of the instrument shaft is defined by the manipulator's hardware joint axes and cannot be changed. Software- and hardware-center manipulators are known in the art and are illustrated in the various patent references above.) In operation of the software-center manipulator assembly 700, movement of a pivotal center of motion 702 of a robotic instrument 704 may be related to an associated port site for minimally invasive surgical access into a patient 706. The manipulator assembly 700 may be mounted to a patient side table, ceiling mount or floor mount, and can compensate for port site motion (e.g., patient breathing) by independently controlling the location of the port site. In the exemplary embodiment of FIG. 7, the port site location can be controlled in response to Cartesian force information at the cannula pivotal center point as sensed by a force sensing cannula 708.

The coordinate frame attached to the cannula 708 is designated as $O_{CAN}$ in FIG. 7. This frame is distinct from a base frame, $O_{BASE}$, at the base of the manipulator assembly 700 and the tip frame, $O_{TIP}$, at the tip of the instrument 704. The Cartesian forces on the cannula 708 can be resolved to control the position of the cannula ($O_{CAN}$). The torques about $O_{CAN}$ are not typically needed for such position control. Some or all of the forces at the port can be resolved using a force sensing system of cannula 708, and optionally at least some of the forces may be resolved using a force sensing system of the instrument 704, the manipulator assembly 700 (e.g., joint torque sensors of the manipulator), or the like.

Additional details related to the software center manipulator assembly 700 can be found, for example, in U.S. Pat. No. 8,004,229 (filed May 19, 2005), the disclosure of which is incorporated herein by reference in its entirety. In some embodiments, a clutch mode may be enabled so that the surgical module 508 of FIG. 5 can be manually adjusted by a technician with the manipulators 504 to technician's manual adjustments. Further details for a clutch mode as applied, for example, to a surgical tool can be found in U.S. Pat. No. 8,823,308.

Figure 8:
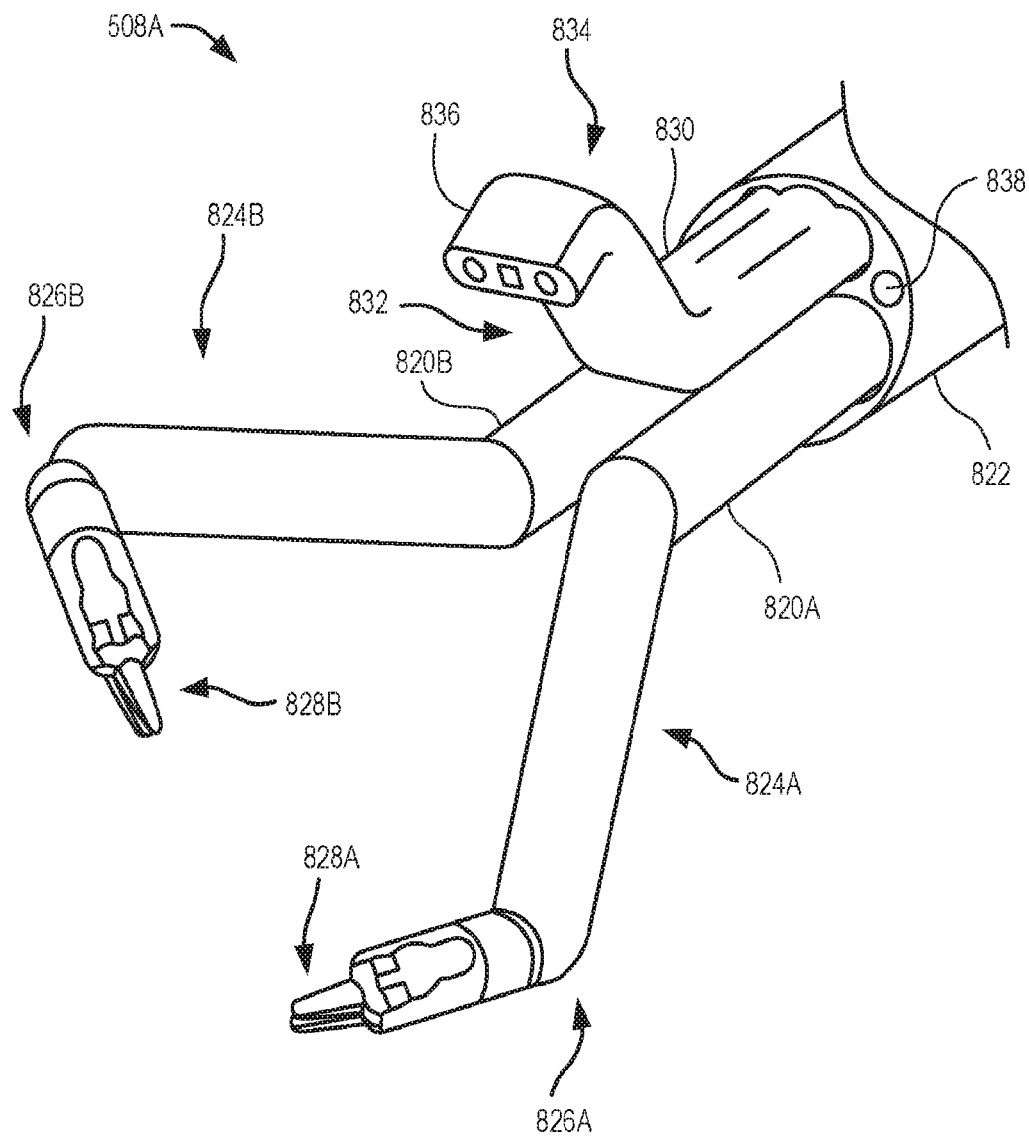
FIG. 8 is a perspective view illustrating surgical tools for a single-port robotically assisted minimally invasive configuration according to an exemplary embodiment.
Figure 9:
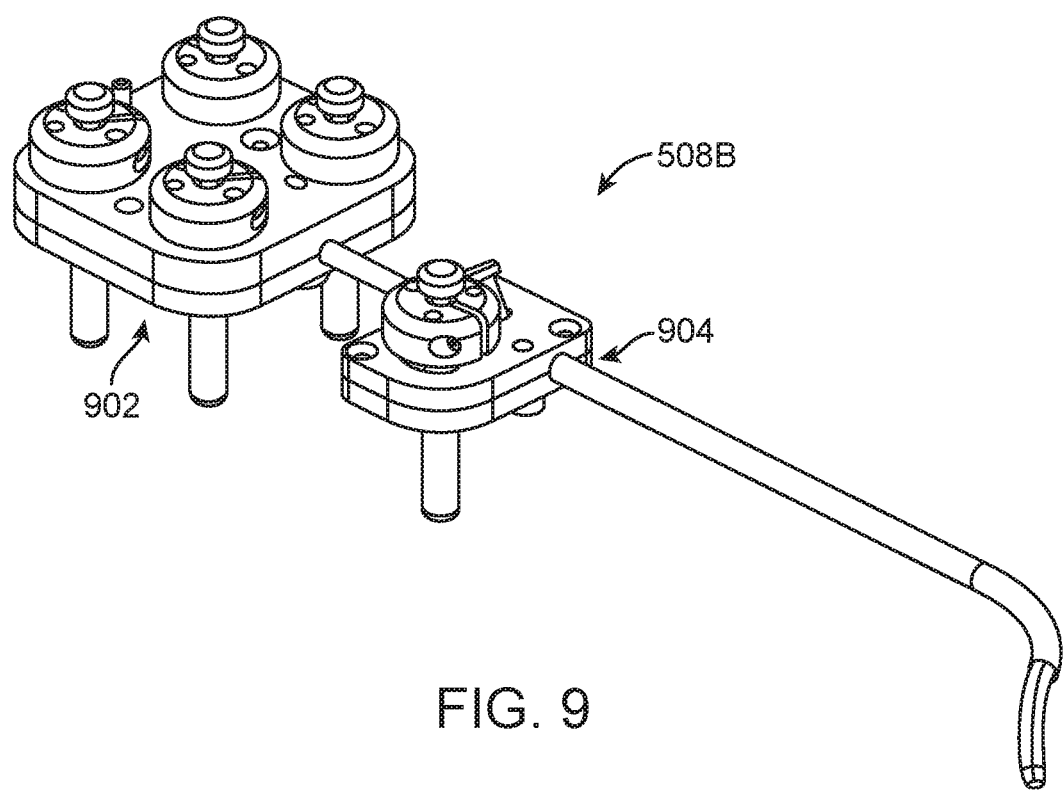
FIG. 9 is a perspective view illustrating surgical tools for a flexible robotically assisted minimally invasive configuration according to an exemplary embodiment.

Tools 508 may be tools used in a single-port procedures or flexible procedures depending on the configuration of surgical module 506. FIG. 8 illustrates an embodiment of surgical tools 508A for a single-port robotically assisted minimally invasive configuration for the present invention. FIG. 9 illustrates an embodiment of surgical tools 508B for flexible robotically assisted minimally invasive configuration for the present invention.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOFs). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae". In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (joint) that provides one or more DOFs between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

In FIG. 8, the tools 508A comprise a surgical instrument assembly that includes multiple surgical instruments. As shown, two independently teleoperated surgical instruments 820A, 820B (each instrument is associated with a separate master 110 at the console 112—e.g. one left hand master for the left instrument and one right hand master for the right instrument) run through and emerge at the distal end of a rigid guide tube 822 (e.g., a sheath). Each instrument 820A, 820B is a 6-DOF instrument, as described above, and includes a parallel motion mechanism 824A, 824B, with wrists 826A, 826B and end effectors 828A, 828B attached. In addition, an independently teleoperated endoscopic imaging system 830 runs through and emerges at the distal end of guide tube 822.

In some embodiments, imaging system 830 also includes a parallel motion mechanism 832, a pitch-only wrist mechanism 834 at the distal end of the parallel motion mechanism 832 (the mechanism may have either one or two DOFs in joint space), and a stereoscopic endoscopic image capture component 836 coupled to wrist mechanism 834. Wrist mechanism 834 may include a yaw DOF. In yet another aspect, the proximal and distal joints in imaging system 830 may be independently controlled. In an illustrative use, parallel motion mechanism 832 heaves and sways image capture component 836 up and to the side, and wrist mechanism 834 orients image capture component 836 to place the center of the field of view between the instrument tips if the instruments are working to the side of the guide tube's extended centerline. In another illustrative use, the distal body segment of imaging system is independently pitched up (in some aspects also independently yawed), and image capture component 836 is independently pitched down (in some aspects also independently yawed). Imaging system 830 may be moved to various places to retract tissue.

FIG. 8 also shows an optional auxiliary channel 838, through which, for example, irrigation, suction, or other surgical items may be introduced or withdrawn. In some aspects, one or more small, steerable devices may be inserted via auxiliary channel 838 to spray a cleaning fluid (e.g., pressurized water, gas) and/or a drying agent (e.g., pressurized air or insufflation gas) on the imaging system's windows to clean them. In another aspect, such a cleaning wand may be a passive device that attaches to the camera before insertion. In yet another aspect, the end of the wand is automatically hooked to the image capture component as the image capture component emerges from the guide tube's distal end. A spring gently pulls on the cleaning wand so that it tends to retract into the guide tube as the imaging system is withdrawn from the guide tube. Additional details related to this embodiment are provided in U.S. Pat. No. 7,725,214.

In FIG. 9, the tools 508B comprise a set of two instruments including a guide instrument 902 and a sheath instrument 904, which are coaxially coupled and independently controllable. These instruments 902, 904 may be flexible and steerable to facilitate surgical operations in the body cavity of a patient. Although not shown in this figure, the guide instrument 902 and the sheath instrument 904 may be coupled to an instrument driver at corresponding interfaces (e.g., including mounting pins and sockets). The guide instrument 902 includes a guide-instrument lumen (e.g., cavity) and the sheath instrument 904 includes a sheath-instrument lumen. The guide instrument 902 may be positioned inside the lumen of the sheath instrument 904, and an elongate working instrument may be positioned in the lumen of the guide-instrument 902 with actuation robotically controlled by the instrument driver. In operation, the guide instrument 902, the sheath instrument 904 and the working instrument may operate as a flexible and steerable instrument assembly. Additional details related to this embodiment are provided in U.S. Pat. No. 8,801,661, the disclosure of which is incorporated herein by reference in its entirety.

Figure 10:
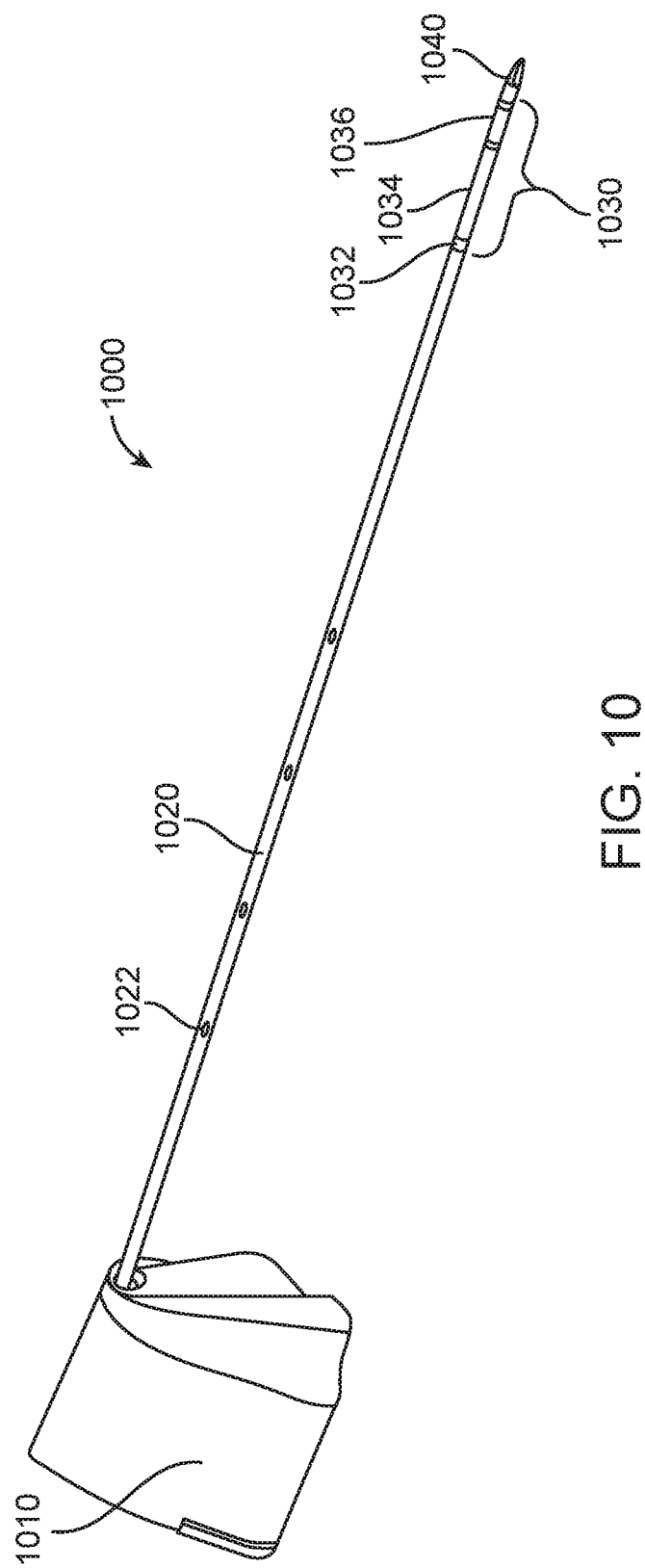
FIG. 10 is a perspective view of another example of a surgical instrument for use in the system of FIG. 1.
Figure 11A:
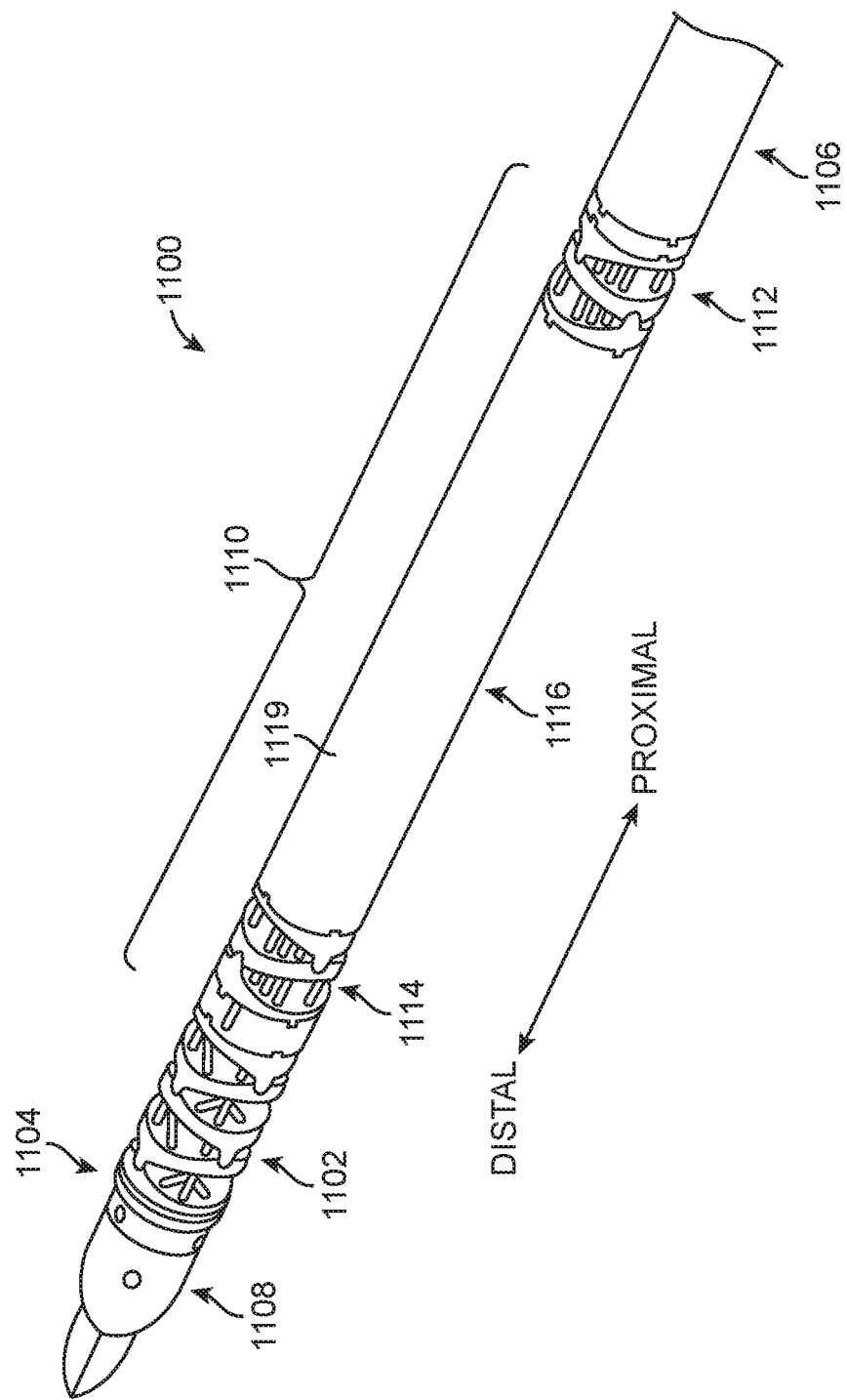
FIG. 11A is a partial perspective view of a distal portion of a surgical instrument including a partial motion mechanism according to an exemplary embodiment.
Figure 11B:
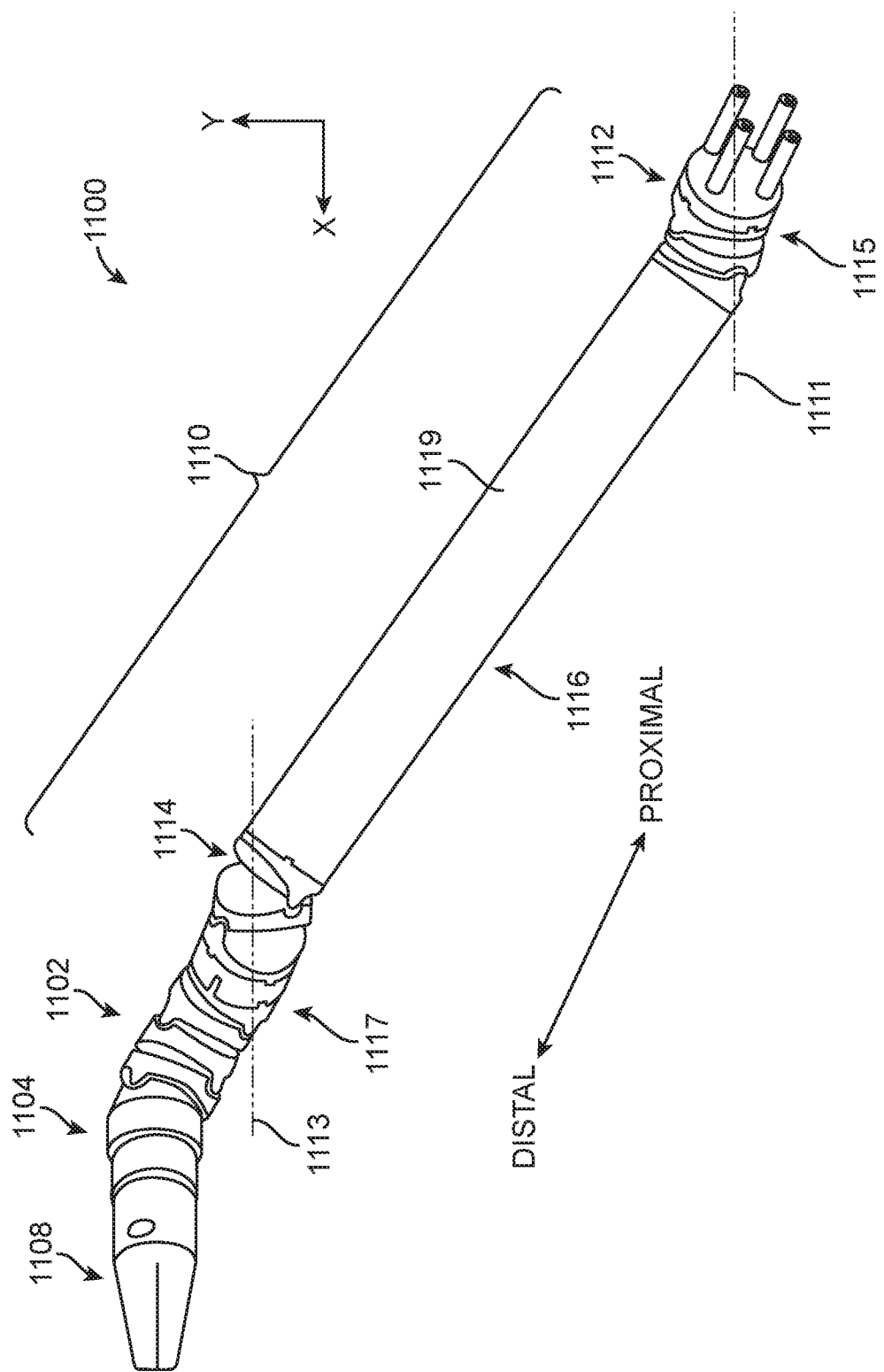
FIG. 11B is a partial perspective view of the distal portion of the surgical instrument of FIG. 11A with the parallel motion mechanism actuated into a deflected configuration.

As illustrated in FIGS. 10, 11A and 11B, additional embodiments may include structural elements that enable or accommodate internal articulations in the shaft of a tool (e.g., shaft 144 of tool 114 of FIG. 3).

In correspondence to the tool 114 of FIG. 3, FIG. 10 shows an exemplary surgical tool (or instrument) 1000 including a transmission or backend mechanism 1010, a main shaft 1020 extending from the backend mechanism 1010, an optional wrist mechanism 1030 at the distal end of main shaft 1020, and an end effector 1040 extending from wrist mechanism 1030 or directly from the shaft 1020. Typically, the wrist mechanism 1030 and end effector 1040 are the components of surgical instrument 1000 that generally move extensively during a medical procedure. In the illustrated embodiment, wrist mechanism 1030 includes a joint 1032 that connects an extended member 1034 to main shaft 1020, and extended member 1034 connects to a multimember wrist 1036 on which end effector 1040 is mounted. Joint 1032 can have two angular degrees of freedom for movement of member 1034, which, as a result of the extended length of member 1034, provides a significant range of spatial motion for wrist 1036 and end effector 1040. Wrist 1036 includes multiple vertebrae that may be independently controlled to provide multiple degrees of freedom for moving and orienting end effector 1040 during a medical procedure. FIG. 10 also illustrates that main shaft 1020 may include one or more cleaning holes 1022, which facilitate cleaning of the interior of instrument 1000. Additional details related to this embodiment are provided in U.S. Pat. No. 9,089,351 (filed Jan. 11, 2013), the disclosure of which is incorporated herein by reference in its entirety.

FIG. 11A shows a distal portion 1100 of a surgical instrument including a parallel motion mechanism 1110 connected to an instrument shaft 1106. The instrument may be a camera instrument or a surgical instrument with an end effector 1108 at a distal end 1104 of the instrument distal portion 1100. The instrument distal portion 1100 may, for example, include a wrist 1102, which may be configured in a variety of ways as described in International Application No. PCT/US2015/015849 (filed Feb. 13, 2015), the disclosure of which is incorporated herein by reference in its entirety. A parallel motion mechanism 1110 may include a straight shaft section 1116 (with an outer casing 1119) that separates a proximal joint mechanism 1112 from a distal joint mechanism 1114. Similarly as in the exemplary embodiments of U.S. Pat. No. 7,942,868 (filed Jun. 13, 2007) and U.S. Pat. No. 9,060,678 (filed Jun. 13, 2007), the disclosures of which are incorporated herein by reference in their entireties, joint mechanisms 1112 and 1114 and the opposite ends of straight section 1116 are coupled together so as to operate in cooperation with each other. According to an exemplary embodiment, proximal joint mechanism 1112 and distal joint mechanism 1114 may include a plurality of connected disks, similar to a wrist. The disks may include, for example, mechanical stops (not shown) to limit the motion of joint mechanisms 1112, 1114, such as in pitch and/or yaw directions.

FIG. 11B shows the instrument distal portion 1100 of FIG. 11A in a deflected configuration according to an exemplary embodiment. As shown in FIG. 11A, parallel motion mechanism 1110 may control the relative orientations of a distal end portion 1117 of parallel motion mechanism 1110 and a proximal end portion 1115 of parallel motion mechanism 1110. As a result, a longitudinal axis 1113 through distal end portion 1117 of parallel motion mechanism 1110 may be substantially parallel to a longitudinal axis 1111 passing through proximal end 1115 of parallel motion mechanism 1110. Longitudinal axis 1111 may also be the longitudinal axis of instrument shaft 1106, not shown in FIG. 11B. Thus, a position of end effector 1108, camera device (not shown), or other component at distal end 1104 of instrument distal portion 1100 may be changed in X-Y space but the orientation of end effector 1108 relative to longitudinal axis 1111 may be maintained (before any motion due to wrist 1102 is accounted for).

Additional details related to the embodiment of FIGS. 11A-11B are provided in International Application No. PCT/US2015/015849.

In some embodiments, flexible and steerable tools 508 (e.g., FIGS. 8, 9, 10, 11A, 11B) may be used with a surgical module 506 where the above-described integration unit 512 is replaced by a system of channels (e.g., including hollow tubes) for deploying tools 508 that are directly controlled by the actuating mechanisms of the manipulators 504. With this interpretation of FIG. 5, the distal portion 510 of each manipulator 504 removably attaches to the surgical module 506 to provide support for the surgical module 506 (e.g., including control for position and orientation). The broken lines of the surgical module 504 in FIG. 5 then represent channels for deploying the tools 508 that are directly controlled by the actuating mechanisms of the manipulators 504. In related embodiments, the surgical module 506 operates as an entry guide for the tools 518 rather than a transmission mechanism for actuation signals. Certain embodiments may combine these features by employing a transmission mechanism for at least one manipulator and an entry guide for at least one other manipulator.

Figure 12:
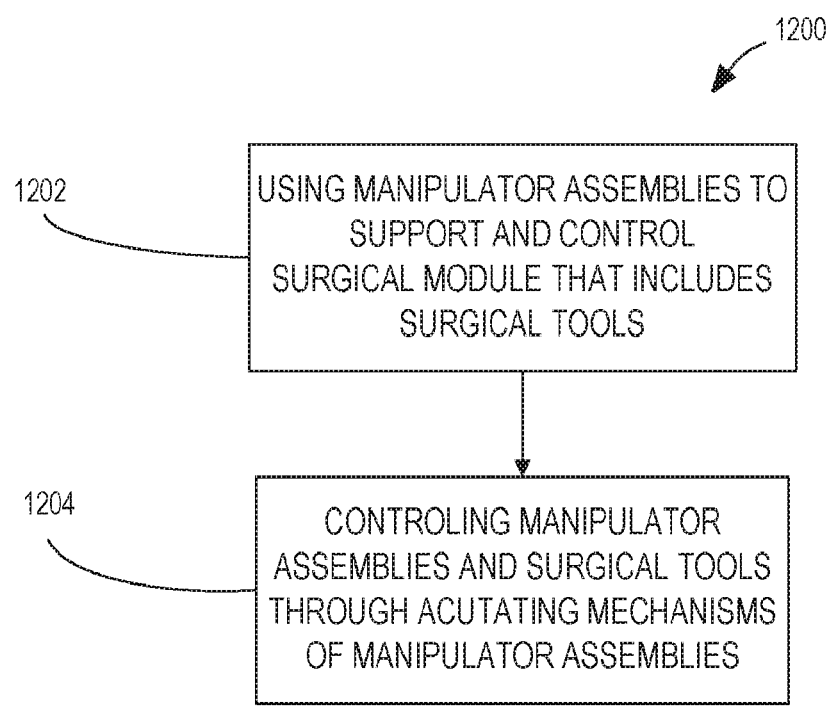
FIG. 12 shows a method of operating a surgical system in accordance with another example embodiment.

Additional mechanisms for operating tools 508 from the surgical module 506 may be employed including manual operation of tools 508 from the surgical module 506 by a technician (e.g., operating a camera mounted on the surgical module 506). In some embodiments, cables and tubing that are conventionally attached to the tools 508 can be attached instead to the surgical module 506, which then relates these connections to the tools 508 (e.g., command signals from the cables, fluid flow from the tubing). These connections can be related, for example, from the input controller at the console 112 or by a technician from controls at the surgical module 506. FIG. 12 shows a method 1200 of operating a computer-assisted medical system (e.g., as in FIGS. 5-6). A first operation 1202 includes using a plurality of manipulator assemblies 504 to support and control a surgical module 506, the surgical module including a plurality of actuating mechanisms configured to control one or more surgical tools 508, and each manipulator assembly of the plurality of manipulator assemblies 504 being removably attached to the surgical module at a distal portion 510 of that manipulator assembly, the distal portion of that manipulator assembly including an actuating mechanism configured to interface with one of the plurality of actuating mechanisms of the surgical module 506. A second operation 1204 includes controlling the manipulator assemblies 504 and the one or more surgical tools 508 through the actuating mechanisms of the plurality of manipulator assemblies 504.

Each manipulator assembly of the plurality of manipulator assemblies 504 may include a plurality of joints from a proximal portion of that manipulator assembly to the distal portion of that manipulator assembly so that joint ranges of the plurality of joints of the plurality of manipulator assemblies correspond to a range of positions for the surgical module 506. Each manipulator assembly of the plurality of manipulator assemblies 504 may include a plurality of joints from a proximal portion of that manipulator assembly to the distal portion of that manipulator assembly so that joint ranges of the plurality of joints of the plurality of manipulator assemblies correspond to a range of positions and orientations for the surgical module 506.

The one or more surgical tools 508 may be configured for use in single-port procedures or in flexible instrument procedures where the tools 508 may be steerable. The one or more surgical tools 508 may include one or more end-effectors and an imaging tool (e.g., a camera). The one or more surgical tools 508 may be flexible and steerable (e.g., including a sheath). The surgical module 506 may include a sheath for deploying the one or more surgical tools 508 at a surgical site of a patient.

Each manipulator assembly of the plurality of manipulator assemblies 504 may be a software-center manipulator assembly that includes a plurality of joints and actuators from a proximal portion of that manipulator assembly to the distal portion of that manipulator assembly so that joint ranges of the plurality of joints of the plurality of manipulator assemblies correspond to a range of positions and orientations for the surgical module. The method 1200 may then further comprise: controlling a position and orientation of the surgical module 506 by controlling the plurality of actuators of the plurality of manipulator assemblies 504.

The one or more surgical tools 508 may include a first surgical tool, and the method 1200 may further comprise: deploying the first surgical tool by controlling a tool-actuation unit that is configured to deploy the first surgical tool through an actuator that changes a position relative to the surgical module for the first surgical tool, the tool actuation unit being operatively connected to one or more of the plurality of actuating mechanisms of the surgical module.

The one or more surgical tools 508 may include a first surgical tool, and the method 1200 may further comprise: controlling the first surgical tool through one or more of the actuating mechanisms of the plurality of manipulator assemblies 504. For example, there need not be a one-to-one mapping between manipulator assemblies 502 and surgical tools 508. A single tool may be controlled by signals from multiple manipulator assemblies 504 (e.g., as specified at the input controller at the console 112). Alternatively, multiple tools may be controlled by signals from a single manipulator assembly 504.

The method 1200 may further comprise: transmitting a plurality of electrical or mechanical signals from each actuating mechanism of the plurality of manipulator assemblies 504 to a corresponding one of the plurality of actuating mechanisms of the surgical module 506.

The method 1200 may further comprise: transmitting mechanical signals from one or more rotatable elements included in a first actuating mechanism of the plurality of manipulator assemblies 504 to one or more corresponding rotatable elements of a first actuating mechanism of the plurality of actuating mechanisms included in the surgical module 506. Additionally or alternatively, prismatic elements can be used to transmit translational mechanical signals.

Figure 13:
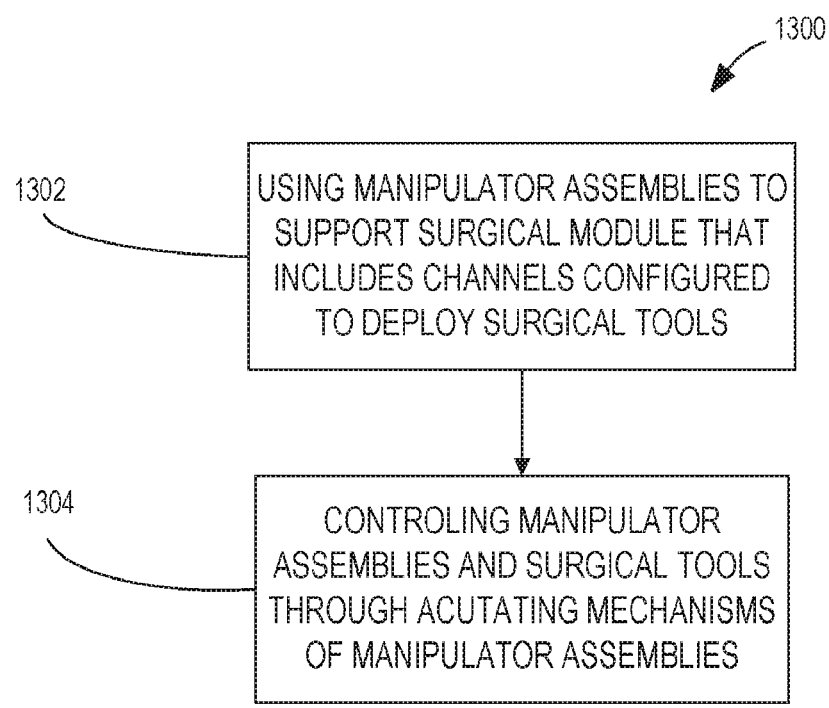
FIG. 13 shows a method of operating a surgical system in accordance with another example embodiment.

FIG. 13 shows a method 1300 of operating a computer-assisted medical system (e.g., as in FIGS. 5-6) when the surgical module includes channels (e.g., including hollow tubes) configured to deploy surgical tools. A first operation 1302 includes using a plurality of manipulator assemblies 504 to support a surgical module 506, the surgical module including a plurality of channels configured to deploy a plurality of surgical tools 508, each manipulator assembly of the plurality of manipulator assemblies 504 being operatively connected to a corresponding surgical tool of the plurality of surgical tools 508, and each manipulator assembly of the plurality of manipulator assemblies 504 being removably attached to the surgical module at a distal portion of that manipulator assembly. A second operation 1304 includes controlling the plurality of manipulator assemblies 504 and the plurality of surgical tools 508 through actuating mechanisms of the plurality of manipulator assemblies 504, the plurality of surgical tools 508 being deployed via the plurality of channels of the surgical module 508.

The surgical tools 508 may be configured for use in single-port procedures or in flexible procedures where the tools 508 may be steerable. The surgical tools 508 may include one or more end-effectors and an imaging tool (e.g., a camera). The one or more surgical tools 508 may be flexible and steerable (e.g., including a sheath).

A first surgical tool may include a flexible and steerable sheath for deploying the first surgical tool at a surgical site of a patient.

Each manipulator assembly of the plurality of manipulator assemblies 504 may include a plurality of joints from a proximal portion of that manipulator assembly to the distal portion of that manipulator assembly so that joint ranges of the plurality of joints of the plurality of manipulator assemblies correspond to a range of positions for the surgical module 506. Each manipulator assembly of the plurality of manipulator assemblies 504 may include a plurality of joints from a proximal portion of that manipulator assembly to the distal portion of that manipulator assembly so that joint ranges of the plurality of joints of the plurality of manipulator assemblies correspond to a range of positions and orientations for the surgical module 506.

Each manipulator assembly of the plurality of manipulator assemblies 504 may be a software-center manipulator assembly that includes a plurality of joints and actuators from a proximal portion of that manipulator assembly to the distal portion of that manipulator assembly so that joint ranges of the plurality of joints of the plurality of manipulator assemblies correspond to a range of positions and orientations for the surgical module. The method 1300 may then further comprise: controlling a position and orientation of the surgical module 506 by controlling the plurality of actuators of the plurality of manipulator assemblies 504.

Figure 14:
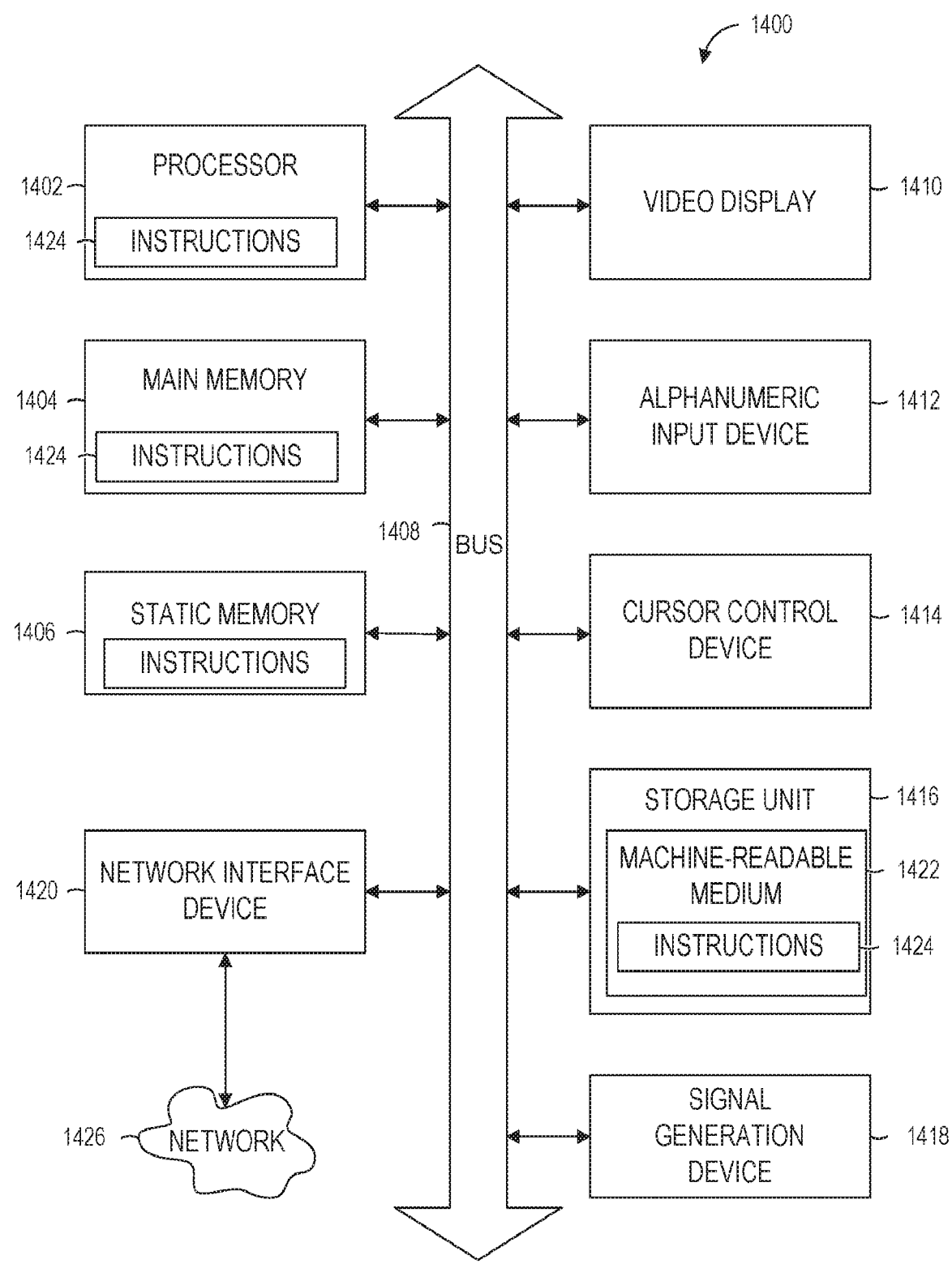
FIG. 14 is a block diagram that shows a computer processing system within which a set of instructions for causing the computer to perform any one of the methodologies discussed herein may be executed.

FIG. 14 shows a machine in the example form of a computer system 1400 within which instructions for causing the machine to perform any one or more of the methodologies discussed here may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a personal digital assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1400 includes a processor 1402 (e.g., a central processing unit (CPU), a graphics processing unit (GPU) or both), a main memory 1404, and a static memory 1406, which communicate with each other via a bus 1408. The computer system 1400 may further include a video display unit 1410 (e.g., a liquid crystal display (LCD) or a cathode ray tube (CRT)). The computer system 1400 also includes an alphanumeric input device 1412 (e.g., a keyboard), a user interface (UI) cursor control device 1414 (e.g., a mouse), a storage unit 1416 (e.g., a disk drive), a signal generation device 1418 (e.g., a speaker), and a network interface device 1420.

In some contexts, a computer-readable medium may be described as a machine-readable medium. The storage unit 1416 includes a machine-readable medium 1422 on which is stored one or more sets of data structures and instructions 1424 (e.g., software) embodying or utilizing any one or more of the methodologies or functions described herein. The instructions 1424 may also reside, completely or at least partially, within the static memory 1406, within the main memory 1404, or within the processor 1402 during execution thereof by the computer system 1400, with the static memory 1406, the main memory 1404, and the processor 1402 also constituting machine-readable media.

While the machine-readable medium 1422 is shown in an example embodiment to be a single medium, the terms "machine-readable medium" and "computer-readable medium" may each refer to a single storage medium or multiple storage media (e.g., a centralized or distributed database, and/or associated caches and servers) that store the one or more sets of data structures and instructions 1424. These terms shall also be taken to include any tangible or non-transitory medium that is capable of storing, encoding or carrying instructions for execution by the machine and that cause the machine to perform any one or more of the methodologies disclosed herein, or that is capable of storing, encoding or carrying data structures utilized by or associated with such instructions. These terms shall accordingly be taken to include, but not be limited to, solid-state memories, optical media, and magnetic media. Specific examples of machine-readable or computer-readable media include non-volatile memory, including by way of example semiconductor memory devices, e.g., erasable programmable read-only memory (EPROM), electrically erasable programmable read-only memory (EEPROM), and flash memory devices; magnetic disks such as internal hard disks and removable disks; magneto-optical disks; compact disc read-only memory (CD-ROM) and digital versatile disc read-only memory (DVD-ROM). However, the terms "machine-readable medium" and "computer-readable medium" are intended to specifically exclude non-statutory signals per se.

The instructions 1424 may further be transmitted or received over a communications network 1426 using a transmission medium. The instructions 1424 may be transmitted using the network interface device 1420 and any one of a number of well-known transfer protocols (e.g., hypertext transfer protocol (HTTP)). Examples of communication networks include a local area network (LAN), a wide area network (WAN), the Internet, mobile telephone networks, plain old telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Certain embodiments are described herein as including logic or a number of components, modules, or mechanisms. Modules may constitute either software modules or hardware-implemented modules. A hardware-implemented module is a tangible unit capable of performing certain operations and may be configured or arranged in a certain manner. In example embodiments, one or more computer systems (e.g., a standalone, client or server computer system) or one or more processors may be configured by software (e.g., an application or application portion) as a hardware-implemented module that operates to perform certain operations as described herein.

In various embodiments, a hardware-implemented module (e.g., a computer-implemented module) may be implemented mechanically or electronically. For example, a hardware-implemented module may comprise dedicated circuitry or logic that is permanently configured (e.g., as a special-purpose processor, such as a field programmable gate array (FPGA) or an application-specific integrated circuit (ASIC)) to perform certain operations. A hardware-implemented module may also comprise programmable logic or circuitry (e.g., as encompassed within a general-purpose processor or other programmable processor) that is temporarily configured by software to perform certain operations. It will be appreciated that the decision to implement a hardware-implemented module mechanically, in dedicated and permanently configured circuitry, or in temporarily configured circuitry (e.g., configured by software) may be driven by cost and time considerations.

Accordingly, the term "hardware-implemented module" (e.g., a "computer-implemented module") should be understood to encompass a tangible entity, be that an entity that is physically constructed, permanently configured (e.g., hardwired), or temporarily or transitorily configured (e.g., programmed) to operate in a certain manner and/or to perform certain operations described herein. Considering embodiments in which hardware-implemented modules are temporarily configured (e.g., programmed), each of the hardware-implemented modules need not be configured or instantiated at any one instance in time. For example, where the hardware-implemented modules comprise a general-purpose processor configured using software, the general-purpose processor may be configured as respective different hardware-implemented modules at different times. Software may accordingly configure a processor, for example, to constitute a particular hardware-implemented module at one instance of time and to constitute a different hardware-implemented module at a different instance of time.

Hardware-implemented modules can provide information to, and receive information from, other hardware-implemented modules. Accordingly, the described hardware-implemented modules may be regarded as being communicatively coupled. Where multiple of such hardware-implemented modules exist contemporaneously, communications may be achieved through signal transmission (e.g., over appropriate circuits and buses) that connect the hardware-implemented modules. In embodiments in which multiple hardware-implemented modules are configured or instantiated at different times, communications between such hardware-implemented modules may be achieved, for example, through the storage and retrieval of information in memory structures to which the multiple hardware-implemented modules have access. For example, one hardware-implemented module may perform an operation and store the output of that operation in a memory device to which it is communicatively coupled. A further hardware-implemented module may then, at a later time, access the memory device to retrieve and process the stored output. Hardware-implemented modules may also initiate communications with input or output devices and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods described herein may be at least partially processor-implemented. For example, at least some of the operations of a method may be performed by one or more processors or processor-implemented modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs)).

Although only certain embodiments have been described in detail above, those skilled in the art will readily appreciate that many modifications are possible without materially departing from the novel teachings of this disclosure. For example, aspects of embodiments disclosed above can be combined in other combinations to form additional embodiments. Accordingly, all such modifications are intended to be included within the scope of this disclosure.

What is claimed is:

1. A computer-assisted medical system comprising:
   a surgical module including a plurality of channels configured to deploy a plurality of surgical tools;
   a plurality of manipulator assemblies that are each operatively connected to a corresponding surgical tool of the plurality of surgical tools, each manipulator assembly having a proximal end portion and a distal end portion, the distal end portion of each manipulator assembly of the plurality of manipulator assemblies being removably attached to the surgical module to physically support the surgical module and to allow of the surgical module to be movably positioned with respect to the proximal end portion of each manipulator assembly;
   an input controller operatively coupled to the plurality of manipulator assemblies via a processor and configured to control the plurality of manipulator assemblies and the plurality of surgical tools through actuating mechanisms of the plurality of manipulator assemblies;
wherein the plurality of surgical tools are deployed via the plurality of channels of the surgical module.

2. The system of claim 1, wherein each of the plurality of surgical tools is configured for use in single-port interventional procedures.

3. The system of claim 2, wherein the plurality of surgical tools includes two end effectors and an imaging tool.

4. The system of claim 2, wherein each of the plurality of surgical tools is flexible and steerable.

5. The system of claim 1, wherein a first surgical tool of the plurality of surgical tools includes a flexible and steerable sheath for deploying the first surgical tool at a surgical site of a patient.

6. The system of claim 1, wherein each manipulator assembly of the plurality of manipulator assemblies includes a plurality of joints from the proximal end portion of that manipulator assembly to the distal end portion of that manipulator assembly so that joint ranges of the plurality of joints of the plurality of manipulator assemblies correspond to a range of positions for the surgical module.

7. The system of claim 1, wherein each manipulator assembly of the plurality of manipulator assemblies includes a plurality of joints from the proximal end portion of that manipulator assembly to the distal end portion of that manipulator assembly so that joint ranges of the plurality of joints of the plurality of manipulator assemblies correspond to a range of positions and orientations for the surgical module.

8. The system of claim 1, wherein:
each manipulator assembly of the plurality of manipulator assemblies is a software-center manipulator assembly that includes a plurality of joints and actuators from the proximal end portion of that manipulator assembly to the distal end portion of that manipulator assembly so that joint ranges of the plurality of joints of the plurality of manipulator assemblies correspond to a range of positions and orientations for the surgical module; and
the input controller is configured to control a position and orientation of the surgical module by controlling the plurality of actuators of the plurality of manipulator assemblies.

9. The system of claim 1, wherein the plurality of channels comprises a plurality of hollow tube channels, and wherein the plurality of surgical tools are physically deployed through the plurality of hollow tube channels.

10. A method of operating a computer-assisted medical system, the method comprising:
using a plurality of manipulator assemblies to physically support and to control a position of a surgical module, the surgical module including a plurality of channels configured to deploy a plurality of surgical tools, each manipulator assembly of the plurality of manipulator assemblies being operatively connected to a corresponding surgical tool of the plurality of surgical tools, and each manipulator assembly of the plurality of manipulator assemblies having a proximal end portion and a distal end portion and being removably attached to the surgical module at the distal end portion of that manipulator assembly; and
controlling, via a processor, the plurality of manipulator assemblies and the plurality of surgical tools through actuating mechanisms of the plurality of manipulator assemblies, the plurality of surgical tools being deployed via the plurality of channels of the surgical module.

11. The method of claim 10, wherein each of the plurality of surgical tools is configured for use in single-port interventional procedures.

12. The method of claim 11, wherein the plurality of surgical tools includes two end effectors and an imaging tool.

13. The method of claim 11, wherein each of the plurality of surgical tools is flexible and steerable.

14. The method of claim 10, wherein a first surgical tool of the plurality of surgical tools includes a flexible and steerable sheath for deploying the first surgical tool at a surgical site of a patient.

15. The method of claim 10, wherein each manipulator assembly of the plurality of manipulator assemblies includes a plurality of joints from the proximal end portion of that manipulator assembly to the distal end portion of that manipulator assembly so that joint ranges of the plurality of joints of the plurality of manipulator assemblies correspond to a range of positions for the surgical module.

16. The method of claim 10, wherein each manipulator assembly of the plurality of manipulator assemblies includes a plurality of joints from the proximal end portion of that manipulator assembly to the distal end portion of that manipulator assembly so that joint ranges of the plurality of joints of the plurality of manipulator assemblies correspond to a range of positions and orientations for the surgical module.

17. The method of claim 10, wherein each manipulator assembly of the plurality of manipulator assemblies is a software-center manipulator assembly that includes a plurality of joints and actuators from the proximal end portion of that manipulator assembly to the distal end portion of that manipulator assembly so that joint ranges of the plurality of joints of the plurality of manipulator assemblies correspond to a range of positions and orientations for the surgical module, and the method further comprises:
controlling a position and orientation of the surgical module by controlling the plurality of actuators of the plurality of manipulator assemblies.

18. The method of claim 10, wherein the plurality of channels comprises a plurality of hollow tube channels, and wherein the plurality of surgical tools are physically deployed through the plurality of hollow tube channels.

19. A computer-assisted medical system comprising:
a surgical module comprising a first driven interface, a second driven interface, and an integration unit comprising a drive interface, wherein a first actuation input at the first driven interface and a second actuation input at the second driven interface drive a first actuation output at the drive interface of the integration unit;
a first manipulator having a proximal end portion and a distal end portion and having a first drive interface coupled to the first driven interface of the surgical module, wherein the first drive interface of the first manipulator drives the first actuation input to the first driven interface of the surgical module; and
a second manipulator having a proximal end portion and a distal end portion and having a second drive interface coupled to the second driven interface of the surgical module, wherein the second drive interface of the second manipulator drives the second actuation input to the second driven interface of the surgical module;
wherein the distal end portion of each of the first and second manipulators is configured to physically support the surgical module and movably position the surgical module with respect to the proximal end portion of each of the first and second manipulators;

wherein the first drive interface of the first manipulator is configured to drive a first surgical instrument when decoupled from the first driven interface of the surgical module;

wherein the second drive interface of the second manipulator is configured to drive a second surgical instrument when decoupled from the second driven interface of the surgical module; and wherein the drive interface of the integration unit is configured to drive a third surgical instrument with the first and second actuation outputs of the drive interface of the integration unit.

20. The computer-assisted medical system of claim 19, wherein the first manipulator comprises a software-center manipulator.

21. The computer-assisted medical system of claim 19, wherein the first surgical instrument comprises a flexible and steerable surgical tool.

\* \* \* \* \*